United States Patent [19]

Asther et al.

[11] Patent Number: 5,153,121

[45] Date of Patent: Oct. 6, 1992

[54] MICROBIAL METHOD FOR PRODUCING LIGNIN PEROXIDASE

[75] Inventors: Marcel Asther, Maurepas; Cecile Capdevila, Versailles; Georges Corrieu, Viroflay, all of France

[73] Assignee: Institut Nationale de la Recherche Agronomique-Inra, Paris, France

[21] Appl. No.: 671,705

[22] PCT Filed: Oct. 2, 1989

[86] PCT No.: PCT/FR89/00506

§ 371 Date: Apr. 1, 1991

§ 102(e) Date: Apr. 1, 1991

[87] PCT Pub. No.: WO90/04021

PCT Pub. Date: Apr. 19, 1990

[30] Foreign Application Priority Data

Oct. 3, 1988 [FR] France ............... 88 12887

[51] Int. Cl.$^5$ ............... C12N 9/08; C12N 1/14; C12R 1/645
[52] U.S. Cl. ............... 435/71.1; 435/41; 435/171; 435/183; 435/189; 435/192; 435/224; 435/254; 435/278; 435/911
[58] Field of Search ............... 435/70.2, 911, 224, 435/171, 278, 189, 192, 41, 183, 71.1, 254

[56] References Cited

U.S. PATENT DOCUMENTS 4,870,016 9/1989 Levesque et al. ............... 435/183
4,882,274 11/1989 Pyne, Jr. et al. ............... 435/183
4,960,699 10/1990 Wood et al. ............... 435/192

FOREIGN PATENT DOCUMENTS 0188931 7/1986 European Pat. Off.
2600077 12/1987 France.
1-027469 1/1989 Japan ............... 435/189

OTHER PUBLICATIONS

Journal of Biotechnology vol. 8, No. 2, Jun. 1988 pp. 163–170, 164–165, 167.
Fems Microbiology Letters vol. 35, 1986, pp. 33–36.
Chemical Abstracts, vol. 106, 1987 245-9; vol. 109, 1988, 333–47; vol. 109, 1988, 484, 165–70; vol. 108, 1988, pp. 541, 393–398.
Biological Abstracts, abstract BR35:264.

*Primary Examiner*—Herbert J. Lilling
*Attorney, Agent, or Firm*—Lackenbach Siegel Marzullo & Aronson

[57] ABSTRACT

Method for producing lignin-peroxydase from the fungus *Phanerochaete chrysosporium*. The method comprises a first step of culture wherein the phospholipids and the emulsified fatty acids are added to the culture medium; a second step during which veratrylic alcohol is added to the culture medium, the culture medium being partially renewed for the second culture step and totally renewed for the third and fourth culture steps, by varying the content of constituents in said medium. Application to the production of lignin-peroxydase with important yields.

10 Claims, 2 Drawing Sheets

MICROBIAL METHOD FOR PRODUCING LIGNIN PEROXIDASE

The present invention relates to an improved method of producing ligninolytic enzyme or lignin peroxidase.

BACKGROUND OF THE INVENTION

In SCIENCE, (1983) 221, pp. 661–663, MING TIEN and T. KENT KIRK have described an extracellular enzyme produced by Phanerochaete chrysosporium Burdsall, which is a basidiomycetes fungus; in the presence of hydrogen peroxide, this enzyme is capable of causing the oxidizing degradation of various model compounds having lignin substructures, as well as the degradation of fir or birch lignin.

This enzyme, called "lignin peroxidase", has been characterized [M. TIEN and T. K. KIRK, PROC. NATL. ACAD. SCI. USA, (1984) vol. 81, pp. 2280–2284] as being a glycoprotein of about 42 kDa.

French patent 2 574 427 claims two novel strains of Phanerochaete chrysosporium Burdsall which are capable of developing a particularly high ligninolytic activity in media of unlimited nitrogen content, whereas the previously known strains produced the ligninolytic enzyme only in a nitrogen-deficient culture medium, the biodegradation process which produced this enzyme also being very slow under these conditions.

According to said patent, the culture medium suitable for promoting the production of lignin peroxidase contains a source of assimilable nitrogen which can be asparagine, ammonium nitrate or ammonium tartrate; it also contains a source of assimilable carbon such as glucose, mannose, starch, melibiose, mannitol, xylose, maltose, adonitol, arabitol, fructose, sorbitol, raffinose, xylitol, D(+)-trehalose or glycerol, the last of these being preferred; it further contains a source of assimilable mineral salts such as iron citrate, $KH_2PO_4$, $ZnSO_4$, $MnSO_4$, $CaCl_2$, $CuSO_4$, NaCl, $FeSO_4$, $CoSO_4$, $Al-K(SO_4)_2$, $H_3BO_3$, $Na_2MoO_4$ or $MgSO_4$.

French patent 2 600 077 proposes significantly increasing the production yields of lignin peroxidase by cultivating the fungus Phanerochaete chrysosporium on a base culture medium supplemented with a stimulant selected from unsaturated fatty acids, natural amino acids and mixtures thereof. The preferred unsaturated fatty acids are oleic acid, linoleic acid, palmitoleic acid and arachidonic acid, preferably in emulsified form, and the preferred natural amino acids are serine, threonine, isoleucine, glycine, valine and tyrosine, but more particularly isoleucine, serine, threonine and glycine. The optimum concentration of oleic acid is about 800 mg/liter or, in the case of emulsified oleic acid, about 400 mg/liter; the optimum concentration of isoleucine is about 6.5 mg/liter.

It should be pointed out that JÄGER et al. (APPLIED AND ENVIRONMENTAL MICROBIOLOGY, Nov. 1985, pp. 1274–1278) have proposed adding a detergent, such as TWEEN 80 or TWEEN 20, to the culture medium of the fungus, in submerged cultures, in order to increase the production of lignin peroxidase in proportions comparable to that currently obtained in stationary cultures. FAISON & KIRK [APPL. ENVIRON. MICROBIOL., (1985) 49, pp. 299–304] and LEISOLA et al. [J. BIOTECHNOL., (1985) 3, pp. 97–107] have reported that the addition of veratryl alcohol, which is a secondary metabolite of Phanerochaete chrysosporium, increases the synthesis of lignin peroxidase.

In an article published in ENZ. MICROBIAL TECHNOL., (1987) 9, pp. 245–249, ASTHER et al. have shown that, in the presence of exogenous oleic acid emulsified by TWEEN 80, there is a significant increase in the production of lignin peroxidase and a considerable reduction in the fermentation time required to reach the maximum enzymic activity.

In a more recent article, published in APPL. MICROBIOL. BIOTECHNOL., (1988) 27, pp. 393–398, ASTHER et al. have reported that the production of lignin peroxidase by the fungus Phanerochaete chrysosporium is further increased when olive oil supplemented with soya azolectin, which constitutes a source of phospholipids, is added to the culture medium.

In a communication delivered at the Annual Meeting of the ASM which took place from May 8 to 13, 1988 in Miami, Fla., United States, ASTHER et al. reported that a maximum production of lignin peroxidase is obtained from cultures of Phanerochaete chrysosporium when culture is carried out at two different temperatures, namely at 37° C. during the growth phase of the mycelium, for the first two days of incubation, and then at 30° C. during the lignin peroxidase production phase.

LEISOLA et al. [q.v. the above-cited article published in J. BIOTECHNOL. in 1985] have identified four hemes containing lignin peroxidase activity in extracellular fluid of three-day-old cultures of Phanerochaete chrysosporium BKM-F-1767, induced by veratryl alcohol. JÄGER et al. [APPL. ENVIRON. MICROBIOL., (1985) 50, pp. 1274–1278] have separated 8 peaks with an absorbance at 409 nm (hemoproteins), assuming that relatively minor differences between the profiles of the proteins simply reflect the age of the cultures.

OBJECTS OF THE INVENTION

The aim of the present invention was to provide a method of producing lignin peroxidase from Phanerochaete chrysosporium under controlled temperature conditions which are different during the growth phase of the mycelium and during the actual lignin peroxidase production phase, and which make it possible to favour the production of the hemoproteins having the maximum lignin peroxidase activity, at the expense of biomass production.

SUMMARY OF THE INVENTION

The present invention relates to a method of producing lignin peroxidase from a fungus known as Phanerochaete chrysosporium, in a culture medium containing activators of the enzyme, such as phospholipids and veratryl alcohol, which method is characterized in that it comprises:

a first step involving the culture of cells of Phanerochaete chrysosporium for an incubation period of about 2 days, in a synthetic culture medium comprising salts of potassium, calcium and magnesium, trace elements (iron, zinc, manganese, copper), an appropriate source of nitrogen, a source of carbon advantageously consisting of glycerol, yeast extract, a source of phospholipids and a source of emulsified fatty acids;

a second step involving culture of the mycelium formed during the first step, for a period of about 3 days (from D3 to D5), in a culture medium which has been partially renewed (advantageously to the extent of about 15%), to which veratryl alcohol—an activator and protector of lignin peroxidase production—has been added, and whose content of phospholipids has been reduced to about 1/7-⅛ of what it was in the culture medium of the first step, the present culture medium not containing emulsified fatty acids;

a third step involving culture at the optimum lignin peroxidase production, i.e. after about 5 days, during which the whole of the culture medium of the second step is replaced with a synthetic culture medium analogous to that of the first step, which contains the same proportion of phospholipids and veratryl alcohol as the culture medium of the second step, and in which the yeast extract, the source of nitrogen and the source of carbon—advantageously consisting of glycerol—have been reduced to ¼ of their content in the culture medium of the first step, these three components together forming a partial regeneration medium for the biomass;

a fourth step consisting in continuing the culture with non-proliferating cells for about 8 days (from D6 to D13), the culture medium being totally renewed every 24 hours and replaced with a medium not containing yeast extract, emulsified fatty acids or glycerol, but containing the activators and protectors of the enzyme production, consisting of veratryl alcohol and phospholipids, in the same proportions as the culture media of the second and third steps; and a fifth step involving separation of the enzyme produced and, if necessary, purification of said enzyme.

The precise strains of the white rot fungus *Phanerochaete chrysosporium* Burdsall employed in this invention have been deposited under the Budapest Treaty at the Collection Nationale de Cultures de Microorganisms (CNCM) at the Pasteur Institute, 25 Rue de Dr. Roux, Paris 75015 France, and are available to the public. These strains of *Phanerochaete chrysosporium* Burdsall bear the identifying numbers CNCM I-398 and CNCM I-399. These same strains and methods for producing them are also described and claimed in European Patent No. 188,931. Another designation at the CNCM, Institute Pasteur, Paris for CNCM I-398 is INA-12, as disclosed by Applicants in Enzyme Microbial Technology, Vol. 13, September 1991 at pp. 727-733.

In one advantageous mode of carrying out the method of producing lignin peroxidase according to the present invention, the first step involving culture of the cells takes place at an incubation temperature of about 37° C., whereas the next steps are carried out at incubation temperatures of about 30° C.

In another advantageous mode of carrying out the method according to the present invention, the first step involving culture of the cells takes place in a culture medium buffered at pH 6.5, whereas the next steps are carried out in a culture medium buffered at pH 5.5.

In yet another advantageous mode of carrying out the method of producing lignin peroxidase according to the present invention, the source of phospholipids advantageously consists of soya azolectin.

In another advantageous mode of carrying out the method of producing lignin peroxidase according to the present invention, the culture medium of the first step has a content of nitrogen source of the order of 1.84 g/liter for a content of carbon source (glycerol) of the order of 10 g/liter, for a content of phospholipids (soya azolectin) of the order of 0.75 g/liter and for a content of yeast extract of 1 g/liter.

In yet another advantageous mode of carrying out the method of producing lignin peroxidase according to the present invention, the culture medium of the second step differs from the culture medium of the first step by its pH (5.5), its reduced content of phospholipids (of the order of 0.1 g/liter) and its content of veratryl alcohol (of the order of 2.5 mM).

In another advantageous mode of carrying out the method of producing lignin peroxidase according to the present invention, the culture medium of the third step differs from the culture medium of the second step by its reduced content of glycerol (about 2.5 g/liter), nitrogen source (in particular about 0.46 g/liter of diammonium tartrate) and yeast extract (0.25 g/liter).

In another advantageous mode of carrying out the method of producing lignin peroxidase according to the present invention, the culture medium of the fourth step differs from the culture medium of the third step in that it does not contain yeast extract, a source of nitrogen or a source of carbon.

In another advantageous mode of carrying out the method of producing lignin peroxidase according to the invention, the third and fourth steps are carried out continuously.

The method according to the present invention affords a considerable increase in the lignin peroxidase productivity and the lignin peroxidase activity compared with all the methods known hitherto. In fact, whereas a lignin peroxidase activity of the order of 22.4 $nKat.ml^{-1}$ is obtained in the case where a culture medium of *Phanerochaete chrysosporium* is supplemented with oleic acid emulsified with Tween 80 at a concentration of 0.04% (weight/volume), and whereas the lignin peroxidase activity is of the order of 33.3 $nKat.ml^{1}$ when the culture medium is supplemented with azolectin as the source of phospholipids and olive oil as the source of lipids, the lignin peroxidase activity can reach 40.6 $nKat.ml^{-1}$ when using the method according to the present invention, in which culture media supplemented successively with phospholipids and emulsified fatty acids, and then with veratryl alcohol and phospholipids, are used at different incubation temperatures of 37° C. for the first culture medium and 30° C. for the second. Moreover, whereas the lignin peroxidase productivity is of the order of 40.6 $nKat.ml^{-1}.day^{-1}$ when using the method according to the invention, it is as low as 4.5 $nKat.ml^{-1}.day^{-1}$ when the culture medium contains oleic acid emulsified with Tween 80, it is 8.3 $nKat.ml^{-1}.d^{-1}$ when the culture medium contains azolectin and olive oil and it is 1.6 $nKat.ml^{-1}.day^{-1}$ when the culture medium contains veratryl alcohol 1 mM, with an incubation temperature of 39° C., as described in the prior art cited.

The FPLC (fast protein liquid chromatography) profiles of extracellular proteins obtained from cultures incubated at 37° C. for the first two days and then at 30° C., with the changes of culture media according to the present invention, show the presence of several hemoproteins, nine of which have lignin peroxidase activity, with a large peak n° 4.

In addition to the foregoing provisions, the invention also includes other provisions which will become apparent from the following description.

PREFERRED EMBODIMENTS OF THE INVENTION

The invention will be understood more clearly with the help of the following additional description referring to the attached drawings, in which:

FIG. 1 shows the flow diagram of the method according to the present invention, and FIG. 2 shows the FPLC profiles of the isoenzymes of lignin peroxidase after 5 days of culture, as a function of the culture conditions.

It must be clearly understood, however, that these drawings and the corresponding descriptive sections are given solely in order to illustrate the subject of the invention, without in any way implying a limitation.

EXAMPLE 1 OF LIGNIN PEROXIDASE PRODUCTION

The microorganism used is the strain *Phanerochaete chrysosporium* INA-12 (CNCM n° I-398).

Cells of *Phanerochaete chrysosporium* INA-12 immobilized on polyurethane foam are treated in the following manner:

1. $6 \times 10^7$ conidiospores are inoculated into a culture medium of the following composition:

| Solution of salts | |
|---|---|
| Potassium dihydrogen phosphate $KH_2PO_4$ | 2 g/l |
| Calcium chloride $CaCl_2.2H_2O$ | 0.14 g/l |
| Magnesium sulphate $MgSO_4.7H_2O$ | 0.7 g/l |
| Solution of trace elements | |
| Iron (ferrous) sulphate $FeSO_4.7H_2O$ | 0.07 g/l |
| Zinc sulphate $ZnSO_4.7H_2O$ | 0.0462 g/l |
| Manganese sulphate $MnSO_4.H_2O$ | 0.035 g/l |
| Copper sulphate $CuSO_4.5H_2O$ | 0.007 g/l |
| Solution of vitamins | |
| Thiamine hydrochloride (vitamin $B_1$) | 0.0025 g/l |
| Source of nitrogen | |
| Ammonium tartrate | 1.84 g/l |
| Source of carbon | |
| Glycerol | 10 g/l |
| Yeast extract | 1 g/l |
| Soya azolectin (phospholipids) | 0.75 g/l |
| Oleic acid emulsified with Tween 80 | 0.4 g/l |
| pH of the culture: 6.5 (the buffer used is 2,2-dimethylsuccinic acid) | |

INTERMEDIATE TEMPERATE: 37° C.

After 100% $O_2$ has been blown in for two minutes, culture is carried out, without agitation, in 150 ml Erlenmeyer flasks containing 30 ml of the abovementioned aqueous culture medium, from D0 to D2 at 37° C.

2. 15% of the above-mentioned total medium is withdrawn and replaced with a culture medium such as described in 1. above, except as regards the yeast extract, the soya azolectin and the emulsified oleic acid, the first and third of which are omitted, as are the glycerol, the diammonium tartrate, the salts, the trace elements and the vitamins, while the content of soya azolectin in the medium is reduced by a factor of 7.5 (0.1 g/liter) and veratryl alcohol (2.5 mM) is added to said medium, the veratryl alcohol and the soya azolectin acting as inductors of lignin peroxidase production. Culture is continued from D3 to D5 inclusive at an incubation temperature of 30° C., which is the optimum temperature for lignin peroxidase production.

3. On D5, the whole of the culture medium is withdrawn and replaced with a culture medium of the following composition:

| Source of nitrogen | |
|---|---|
| Diammonium tartrate | 0.46 g/l |
| Source of carbon | |
| Glycerol | 2.5 g/l |

-continued

| Yeast extract | 0.25 g/l |
|---|---|
| Soya azolectin | 0.1 g/l |
| Veratryl alcohol | 2.5 mM |

The veratryl alcohol and the soya azolectin present in this medium act as inductors and protectors of the lignin peroxidase, as in the culture medium used in step 2. above, and the glycerol, the ammonium tartrate and the yeast extract together form a regeneration medium for the biomass. The pH of the culture medium is adjusted to 5.5 and the incubation temperature is 30° C. The glycerol, the source of nitrogen and the yeast extract act on the production of biomass and not on the production of enzyme, which is why they are present in the regeneration medium. However, their concentrations are reduced to 25% of what they are in the culture medium of step 1. above, so as to limit the production of biomass in proportions which do not jeopardize production of the enzyme.

4. From D6, the whole of the culture medium is withdrawn every 24 hours and replaced with a culture medium of the same composition as that used in step 2. above, and culture is continued up to D13 at 30° C. and at pH 5.5.

FIG. 1 attached represents a diagram of the method of producing lignin peroxidase by using non-proliferating cells of *Phanerochaete chrysosporium*, according to the present invention.

In this diagram:

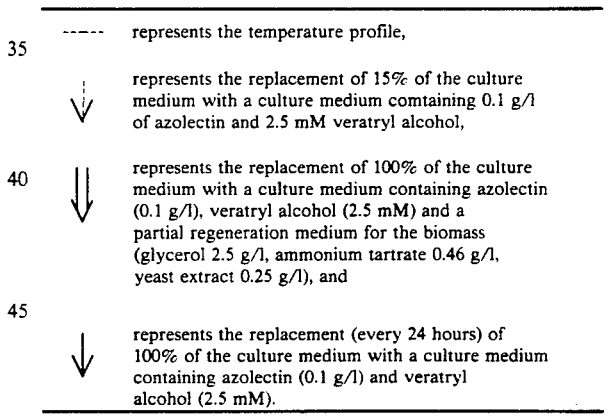

- - - - represents the temperature profile,

↓ represents the replacement of 15% of the culture medium with a culture medium comtaining 0.1 g/l of azolectin and 2.5 mM veratryl alcohol, ⇓ represents the replacement of 100% of the culture medium with a culture medium containing azolectin (0.1 g/l), veratryl alcohol (2.5 mM) and a partial regeneration medium for the biomass (glycerol 2.5 g/l, ammonium tartrate 0.46 g/l, yeast extract 0.25 g/l), and ↓ represents the replacement (every 24 hours) of 100% of the culture medium with a culture medium containing azolectin (0.1 g/l) and veratryl alcohol (2.5 mM).

5. The cultures obtained are harvested and filtered on a glass fibre filter. The supernatant is dialyzed overnight against distilled water. The extracellular medium is then concentrated to 1/10 of its initial volume by ultrafiltration through an Amicon YM10 membrane.

The proteins contained in the concentrated fluid are determined by FPLC (fast protein liquid chromatography) using a PHARMACIA LCC 500 chromatograph equipped with a Mono QHR 515 anion exchange column, with a gradient of NaCl in 10 mM sodium cacodylate (pH 5.9). The FPLC profiles of the isoenzymes of lignin peroxidase obtained are shown in FIG. 2 attached, in which FIG. 2A represents the profiles of extracellular proteins of *Phanerochaete chrysosporium* INA-12 under standard culture conditions without renewal of the culture medium, the incubation temperature being 37° C.;

Figure 1:
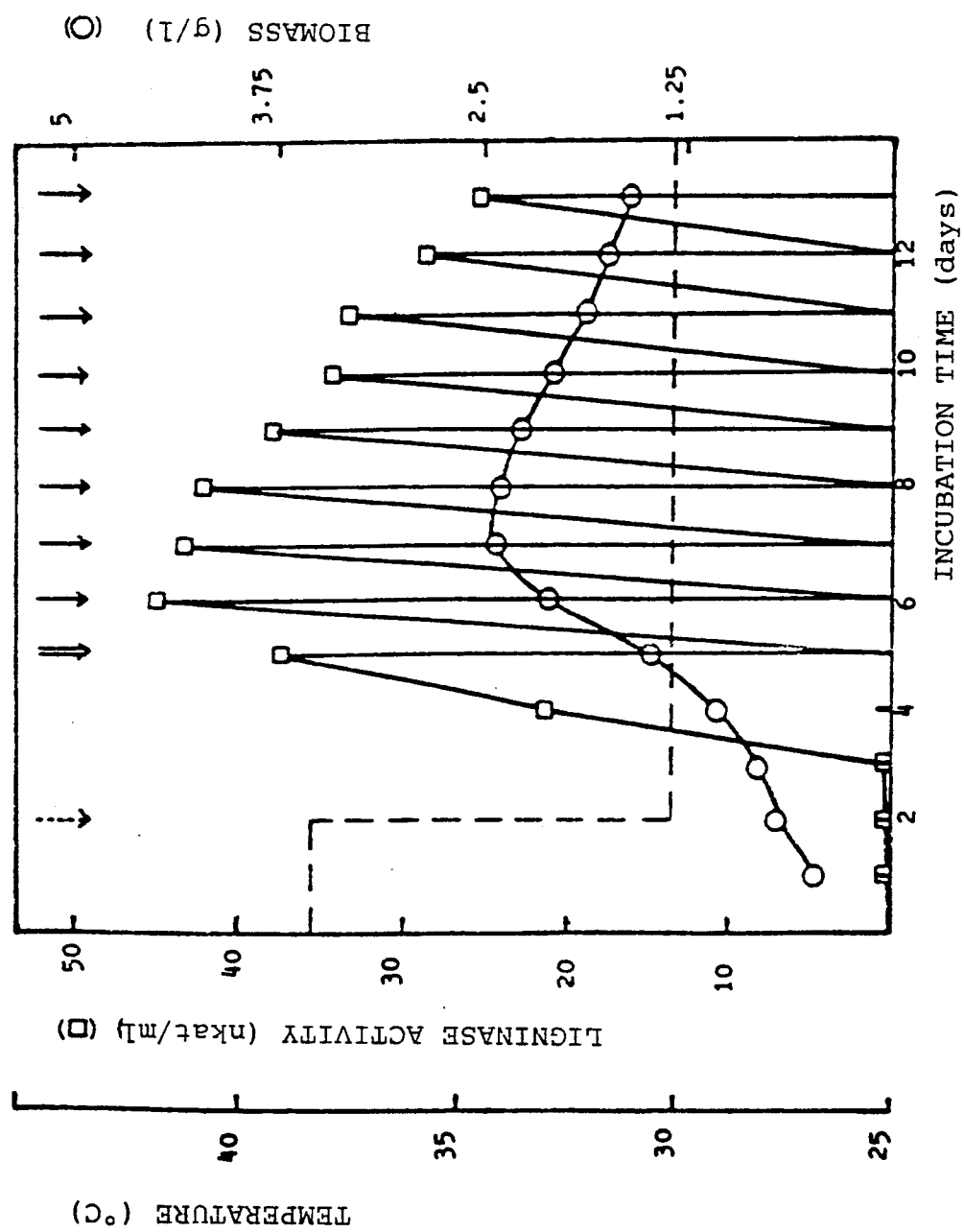
Figure 2:
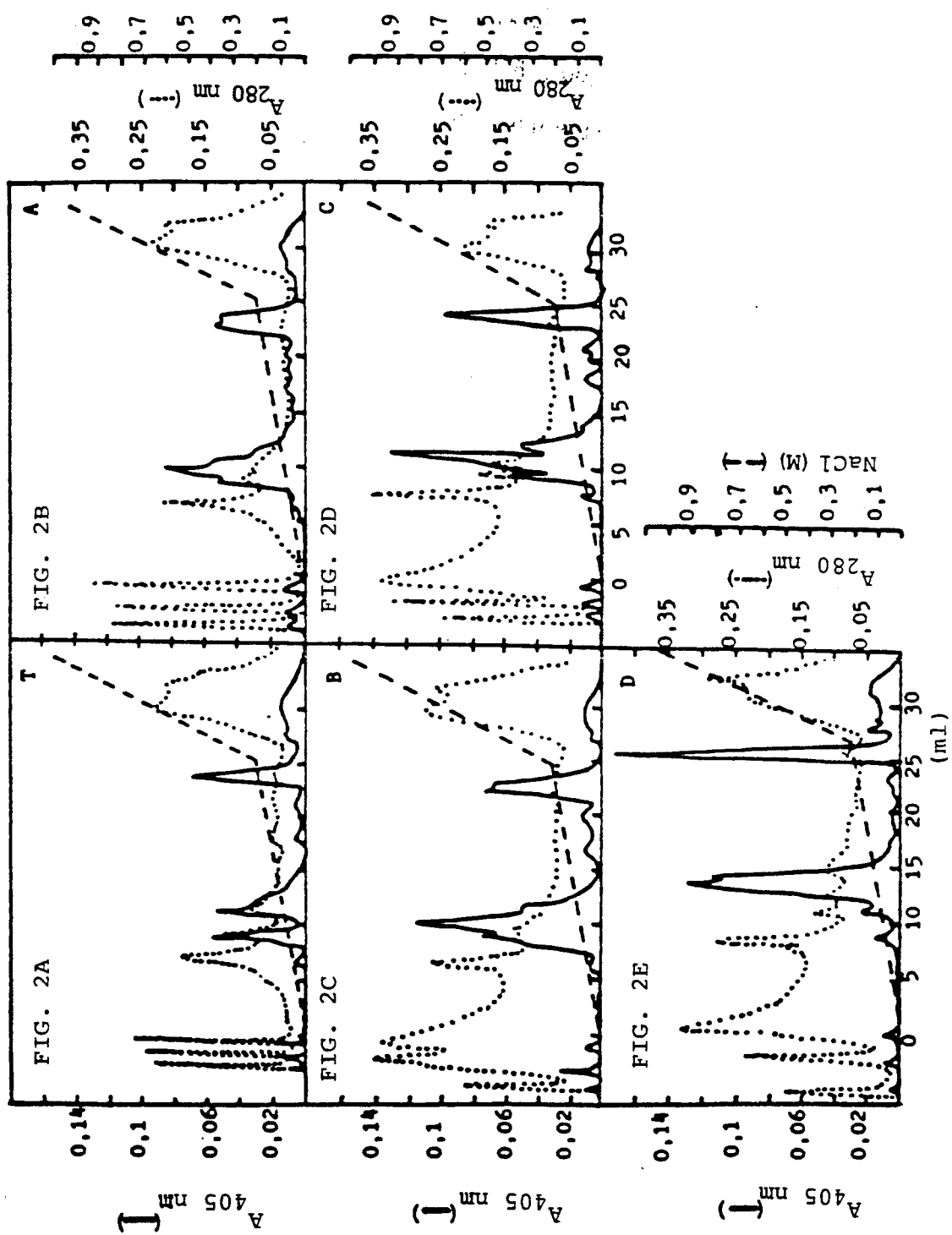
FIG. 2B represents said protein profiles obtained with renewal of the atmosphere (100% oxygen) after two days of culture.
FIG. 2C represents said protein profiles obtained with renewal of the atmosphere with oxygen and changing of 15% of the medium with 2.5 mM veratryl alcohol after two days of culture.

FIG. 2D represents said protein profiles obtained with renewal of the atmosphere with oxygen and changing of 15% of the medium with 2.5 mM veratryl alcohol and 0.1 g/l of azolectin after two days of culture; and FIG. 2E represents said protein profiles obtained with renewal of the atmosphere with oxygen and changing of 15% of the medium with 2.5 mM veratryl alcohol and 0.1 g/l of azolectin, and changing of the incubation temperature from 37° C. to 30° C. after two days of culture. The absorbance at 405 nm is represented by solid lines and the absorbance at 280 nm by broken lines; the sloping line represents the gradient of NaCl.

These profiles show that the extracellular fluid contains several hemoproteins, six of which have lignin peroxidase activity; these hemoproteins correspond to peaks 1, 2, 3, 4, 5, 6, 7, 8 and 9. 80% of the lignin peroxidase activity is associated with peaks 7, 8 and 9. The cultures whose incubation temperatures were successively 37° C. and then 30° C., and those whose incubation temperature was 30° C. only, show an increase in the proportion of peak 4.

EXAMPLE 2 OF LIGNIN PEROXIDASE PRODUCTION

The conditions of Example 1 are repeated, 100 ml of medium being introduced into a 250 ml Erlenmeyer flask; an enzyme production of 46.4 nKat/ml is obtained.

EXAMPLE 3 OF LIGNIN PEROXIDASE PRODUCTION

The microorganism used is also the strain *Phanerochaete chrysosporium* INA-12 (CNCM n° I-398).

Cells of *Phanerochaete chrysosporium* INA-12 immobilized on polyurethane foam are treated as in step 1 of Example 1.

The reactor is inoculated with $2.10^5$ spores/ml. There is direct immobilization in situ in the reactor.

The medium is fed continuously with oxygen introduced through a central shaft, where the agitating turbine (200 rpm) is also situated. The $O_2$ concentration is regulated to about 60% of saturation of the medium with air. The cells of *Phanerochaete chrysosporium* immobilized on the polyurethane foam are placed at the periphery of the bioreactor, around the central shaft.

Steps 2 to 5 are identical to those of Example 1.

The enzyme titre obtained reaches 25 nKat/ml/day.

The method according to the present invention makes it possible to control the production of lignin peroxidase and consequently affords the possibility of producing this enzyme on an industrial scale.

As is apparent from the foregoing description, the invention is in no way limited to those modes of execution, embodiments and modes of application which have now been described more explicitly; on the contrary, it encompasses all the variants thereof which may occur to those skilled in the art, without deviating from the framework or the scope of the present invention.

We claim:

1. A method for producing lignin peroxidase from a strain of fungus known as Phanerochaete chrysosporium CNCM I-398 and 399, in a culture medium containing activators and protectors of the enzyme, chosen from the group consisting of phospholipids and veratryl alcohol and mixtures thereof comprising the steps of:

a) culturing cells of Phanerochaete chrysosporium for an incubation period of about two days, in a synthetic culture medium comprising salts of potassium, calcium and magnesium, and trace elements selected from the group consisting of iron, zinc, magnesium, copper and mixtures thereof, an appropriate source of nitrogen, an appropriate source of carbon, a source of phospholipids, and a source of emulsified fatty acids, which first step takes place at an incubation temperature of about 37° C.±0.5° C., the culture medium being buffered at about pH 6.5;

b) culturing the mycelium formed during step a), for a period of about three more days, in a culture medium which has been partially renewed by adding veratryl alcohol together with phospholipids, and whose content of phospholipids has been reduced to 1/7-⅛ of what it was in the culture medium of step a), which present culture medium free from emulsified fatty acids and is buffered at about pH 5.5, at an incubation temperature of about 30° C.±0.5° C.;

c) replacing the culture medium of step b) with a synthetic culture medium analogous to that of the step a) having salts, a source of nitrogen, a source of carbon, a source of phospholipids and a source of emulsified fatty acids having the same proportion of phospholipids and veratryl alcohol as the culture medium of step b), and in which the yeast extract, the source of nitrogen and the source of carbon have been reduced to ¼ of their content in the culture medium of step a), these three components together forming a partial regeneration medium, the incubation temperature being about 30° C.±0.5° C. and the pH of the culture medium being about 5.5;

d) continuing the culture with non-proliferating cells for eight days, the culture medium being totally renewed every day and replaced with a medium free of yeast extract, emulsified fatty acids, and glycerol, but containing the activators and protectors of the enzyme production, comprising veratryl alcohol and phospholipids, in the same proportions as the culture media of steps b) and c), the pH and the incubation temperature being the same as during steps b) and c);

e) separating the enzyme produced and, f) purifying said enzyme.

2. A method according to claim 1, wherein the source of phospholipids comprises soya azolectin.

3. A method according to claim 1, wherein the culture medium of step a) has a content of nitrogen source of about 1.84 g/liter, a content of carbon of about 10 g/liter, a content of phospholipids of about 0.75 g/liter, and a content of yeast extract of about 1 g/liter.

4. A method according to claim 1, wherein the culture medium of step b) differs from the culture medium of step a) by its lower pH, its reduced content of phospholipids, and its content of veratryl alcohol.

5. A method according to claim 1, wherein the culture medium of step c) differs from the culture medium of step b) by its reduced content of glycerol, nitrogen source, and yeast extract.

6. A method according to claim 1, wherein the culture medium of step d) differs from the culture medium of step c) in that it is free from yeast extract, a source of nitrogen, and a source of carbon.

7. A method according to claim 1, wherein the cultures obtained are harvested and separated by filtration, after which the extracellular medium obtained is concentrated in order to collect the desired lignin peroxidase.

8. The method according to claim 3, wherein the source of carbon is glycerol.

9. The method according to claim 3, wherein the source of phospholipid is soya azolectine.

10. The method according to claim 1, wherein the renewal of the culture medium in step b) is about 15 percent.

* * * * *